US011147989B2

United States Patent
Cox et al.

(10) Patent No.: US 11,147,989 B2
(45) Date of Patent: Oct. 19, 2021

(54) COMPENSATING FOR TARGET ROTATION WITH A COLLIMATION SYSTEM

(71) Applicant: Accuray Incorporated, Sunnyvale, CA (US)

(72) Inventors: Andrea Cox, Madison, WI (US); Eric Schnarr, McFarland, WI (US)

(73) Assignee: Accuray Incorporated, Sunnyvale, CA (US)

( * ) Notice: Subject to any disclaimer, the term of this patent is extended or adjusted under 35 U.S.C. 154(b) by 85 days.

(21) Appl. No.: 16/013,800

(22) Filed: Jun. 20, 2018

(65) Prior Publication Data
US 2019/0388711 A1 Dec. 26, 2019

(51) Int. Cl.
*A61N 5/10* (2006.01)

(52) U.S. Cl.
CPC ......... *A61N 5/1075* (2013.01); *A61N 5/1036* (2013.01); *A61N 5/1039* (2013.01); *A61N 5/1045* (2013.01); *A61N 5/1069* (2013.01); *A61N 5/1081* (2013.01); *A61N 5/1083* (2013.01); *A61N 2005/1055* (2013.01); *A61N 2005/1059* (2013.01); *A61N 2005/1061* (2013.01)

(58) Field of Classification Search
CPC .............. A61N 5/1075; A61N 5/1036; A61N 5/1039; A61N 5/1045; A61N 5/1069; A61N 5/1081; A61N 5/1083; A61N 2005/1055; A61N 2005/1059; A61N 2005/1061
See application file for complete search history.

(56) References Cited

U.S. PATENT DOCUMENTS

| | | | |
|---|---|---|---|
| 8,767,917 B2* | 7/2014 | Ruchala | A61N 5/103 378/65 |
| 2004/0184579 A1* | 9/2004 | Mihara | A61N 5/10 378/65 |
| 2005/0197564 A1* | 9/2005 | Dempsey | G01R 33/34061 600/411 |

(Continued)

FOREIGN PATENT DOCUMENTS

| | | |
|---|---|---|
| EP | 1419801 A1 | 5/2004 |
| WO | 2014043172 A1 | 3/2014 |

(Continued)

OTHER PUBLICATIONS

Altenstein et al., "A novel 2D binary collimator for IMRT dose delivery: dosimetric characterization using Monte Carlo simulations", Phys. Med. Biol. 57 N345-N364 (Year: 2012).*

(Continued)

*Primary Examiner* — Blake C Riddick
(74) *Attorney, Agent, or Firm* — Womble Bond Dickinson (US) LLP

(57) ABSTRACT

A method includes detecting a potential setup error in a radiation treatment delivery session of a radiation treatment delivery system, wherein the setup error corresponds to a change in a current position of a treatment target relative to a prior position of the treatment target, and wherein the change includes a rotation relative to the prior position of the treatment target. The method further includes modifying, by a processing device, one or more planned leaf positions of a multileaf collimator (MLC) of a linear accelerator (LINAC) of the radiation treatment delivery system to compensate for the potential setup error corresponding to the rotation of the prior position of the treatment target.

24 Claims, 8 Drawing Sheets

(56) References Cited

U.S. PATENT DOCUMENTS

| | | | |
|---|---|---|---|
| 2007/0165779 A1* | 7/2007 | Chen | A61N 5/1049 378/65 |
| 2008/0159478 A1 | 7/2008 | Keall | |
| 2009/0116616 A1* | 5/2009 | Lu | A61N 5/1049 378/65 |
| 2010/0054409 A1* | 3/2010 | Bose | G06F 19/3481 378/65 |
| 2010/0268073 A1* | 10/2010 | Falco | A61N 5/1049 600/427 |
| 2011/0112351 A1* | 5/2011 | Fordyce, II | A61N 5/103 600/1 |
| 2013/0121469 A1* | 5/2013 | Sobering | A61N 5/1031 378/65 |
| 2013/0142310 A1* | 6/2013 | Fahimian | A61N 5/103 378/65 |
| 2013/0163723 A1 | 6/2013 | Tacke | |
| 2014/0070115 A1* | 3/2014 | Oster | A61N 5/1045 250/492.1 |
| 2014/0100408 A1* | 4/2014 | Yan | A61N 5/107 600/1 |
| 2016/0287906 A1* | 10/2016 | Nord | A61N 5/103 |
| 2017/0128750 A1* | 5/2017 | Filiberti | A61N 5/1075 |
| 2018/0056091 A1* | 3/2018 | Jordan | A61N 5/1039 |
| 2018/0361172 A1* | 12/2018 | Zhang | A61N 5/1082 |

FOREIGN PATENT DOCUMENTS

| | | |
|---|---|---|
| WO | 2017106746 A1 | 6/2017 |
| WO | 2018044718 A1 | 3/2018 |

OTHER PUBLICATIONS

International Search Report and Written Opinion for International Application PCT/US2019/037665, dated Oct. 4, 2019.

Transmittal of International Preliminary Report on Patentability dated Dec. 30, 2020, for International Application No. PCT/US2019/037665, filed Jun. 18, 2019, pp. 8.

* cited by examiner though less comfortable for the patient.

COMPENSATING FOR TARGET ROTATION WITH A COLLIMATION SYSTEM

TECHNICAL FIELD

The present disclosure relates to compensating for target motion in a radiation treatment system.

BACKGROUND

In radiation treatment, doses of radiation delivered via a radiation treatment beam from a source outside a patient's body are delivered to a target region in the body, in order to destroy tumorous cells. Typically, the target region consists of a volume of tumorous tissue. Throughout radiation treatment, the location of a target within the body may shift, thus requiring modifications to planned treatments to ensure adequate treatment dosage to the target, while minimizing treatment dosage to surrounding areas. While some types of target motion may be compensated for using only straightforward adjustments to the directionality of the treatment beam, others, like rotational movements, may require more in-depth compensation techniques.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
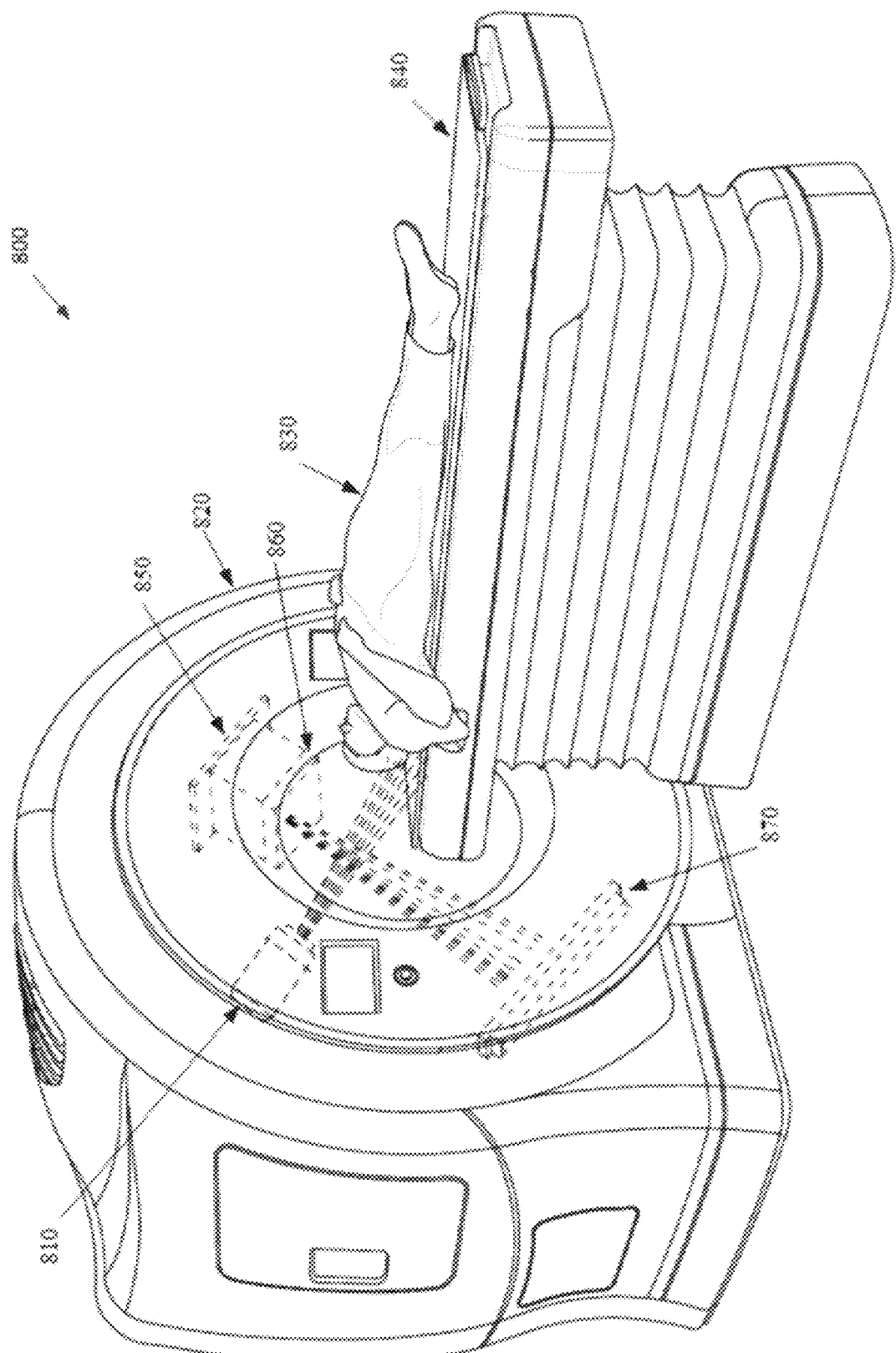
FIG. 1A illustrates a helical radiation delivery system, in accordance with embodiments described herein.

Described herein are embodiments of methods and apparatus for compensating for target rotation with a collimation system.

In some radiation treatment systems, the ring-gantry geometry of such systems may make it difficult to compensate radiation treatment delivery for rotational movement (e.g., pitch, yaw, and roll) of a target. In some systems, a six-dimensional (6D) treatment couch on which the patient resides, which is capable of moving in all six spatial and angular directions (i.e. x-direction, y-direction, z-direction, roll, pitch, and yaw), may be used to compensate for rotational movement of a target. Disadvantageously, some radiation delivery systems require that the treatment couch (also referred to as a table) be stationary in at least the pitch and yaw directions of target motion, as the ring-gantry is incapable of movement in those directions.

Furthermore, even systems that include a 6D treatment couch may suffer from a number of issues related to rotational movement of a target. First, such systems can be prohibitively expensive. Second, the rotational movement of a 6D treatment couch can be uncomfortable for the patient, thus leading to a negative user experience. Third, such systems may lead to unexpected additional motion of the target, thus requiring additional time, processing power, and computing resources to remedy.

In some radiation treatment systems, the collimators that shape the radiation beam are capable of rotation, allowing rotation of the treatment target to be compensated for by corresponding rotation of the collimation components. Such a design may add complexity to the design of the collimation system, and not all treatment delivery systems have the capability.

A target rotation compensation system, such as that described herein, would therefore be desirable in radiation treatment systems, such as a gantry-based radiation treatment system. In addition to overcoming the problems noted above, the embodiments described herein may be used with existing collimation hardware to automatically compensate for rotational (e.g., pitch, yaw, and roll) setup errors.

The term "target" may refer to one or more fiducials near (within some defined proximity to) a treatment area (e.g., a tumor). In another embodiment, a target may be a bony structure. In yet another embodiment a target may refer to soft tissue of a patient. A target may be any defined structure or area capable of being identified and tracked, as described herein.

Embodiments of the present disclosure compensate for target rotation with a collimator, such as multi-leaf collimator (MLC), by changing planned MLC leaf positions during treatment to move the effective location of the treatment beam, rather than by moving the couch to change the patient orientation or by rotating the entire collimator. This avoids the complexity and expense of a having a rotating collimator, and has the advantage of not requiring the couch to be rotated, which can both be uncomfortable for the patient, and also lead to unexpected additional motion of the target.

Using existing collimation hardware to automatically compensate for pitch and yaw setup errors, as described herein, provides valuable additional functionality to the radiation treatment systems, with a solution that would be less expensive and/or more comfortable for patients than current solutions in the industry.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multi-leaf collimator (MLC) 860. The MLC includes a housing that houses multiple leaves that are movable to adjust an aperture of the MLC to enable shaping of the treatment beam. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
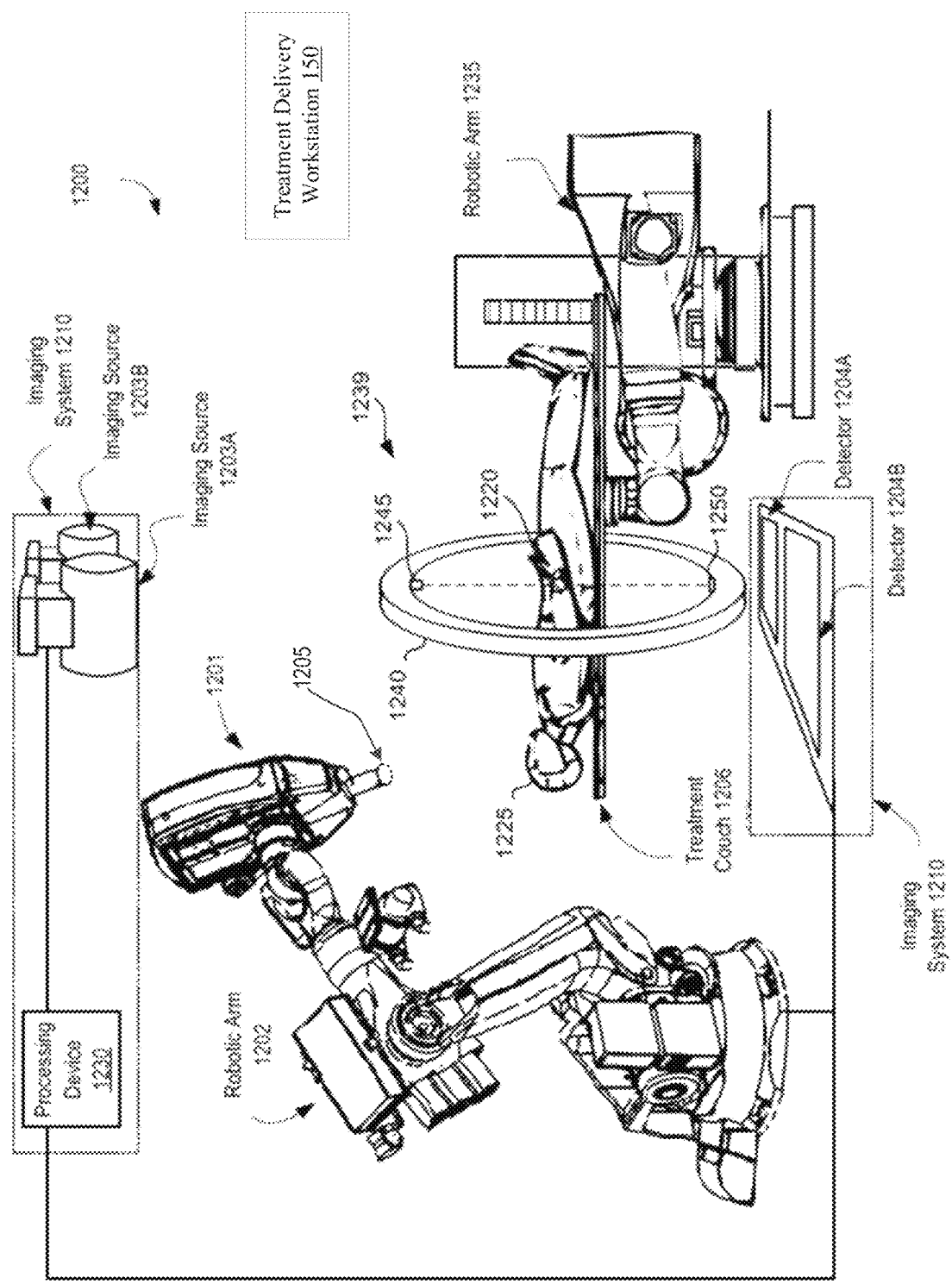
FIG. 1B illustrates a radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 in mounted in front of the LINAC to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
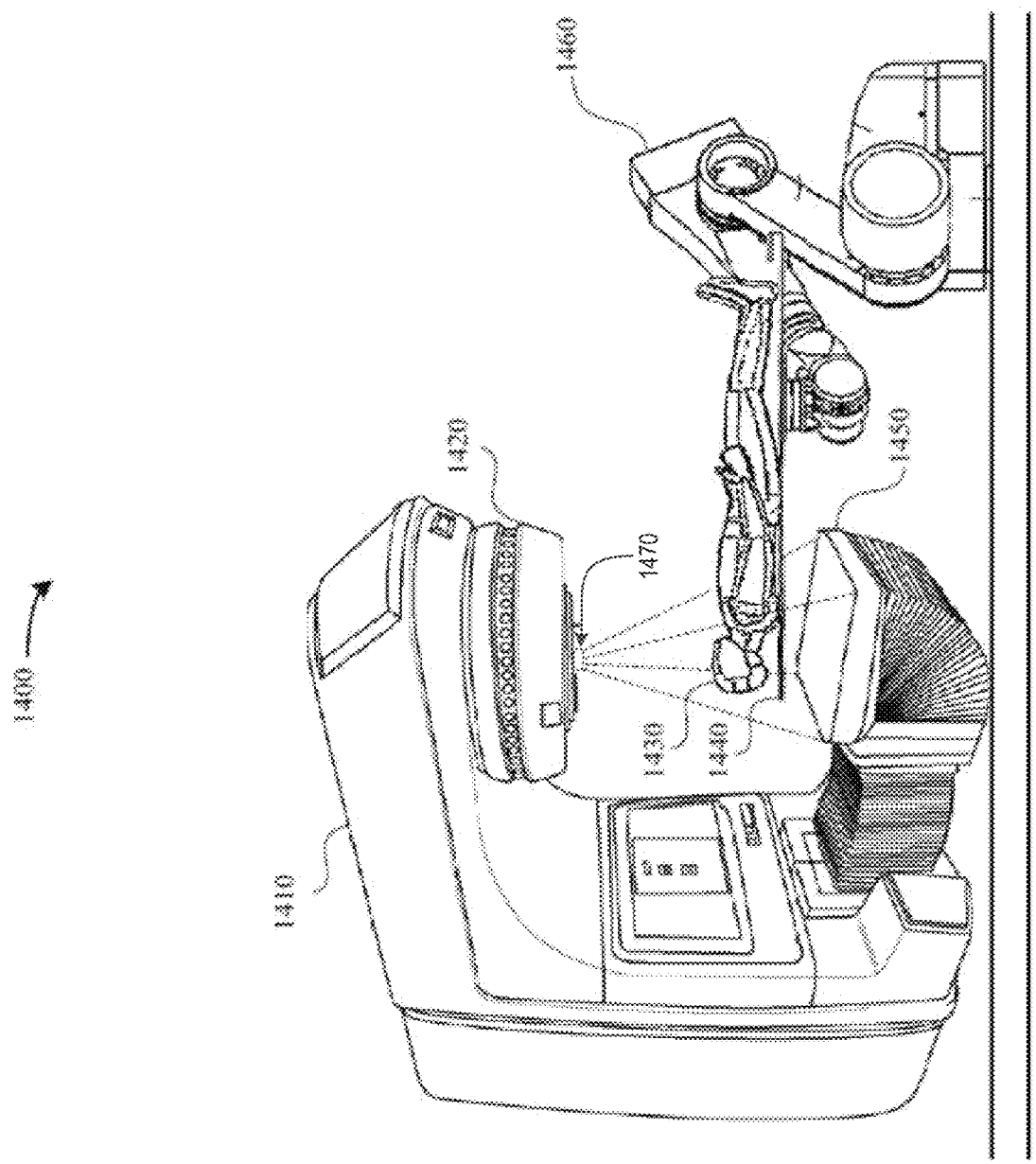
FIG. 1C illustrates a c-arm gantry-based radiation treatment system, in accordance with embodiments described herein.

FIG. 1C. Illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a gantry 1410, a LINAC 1420, an MLC 1470 in front of the LINAC 1420 to shape the beam, and a portal imaging detector 1450. The gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2:
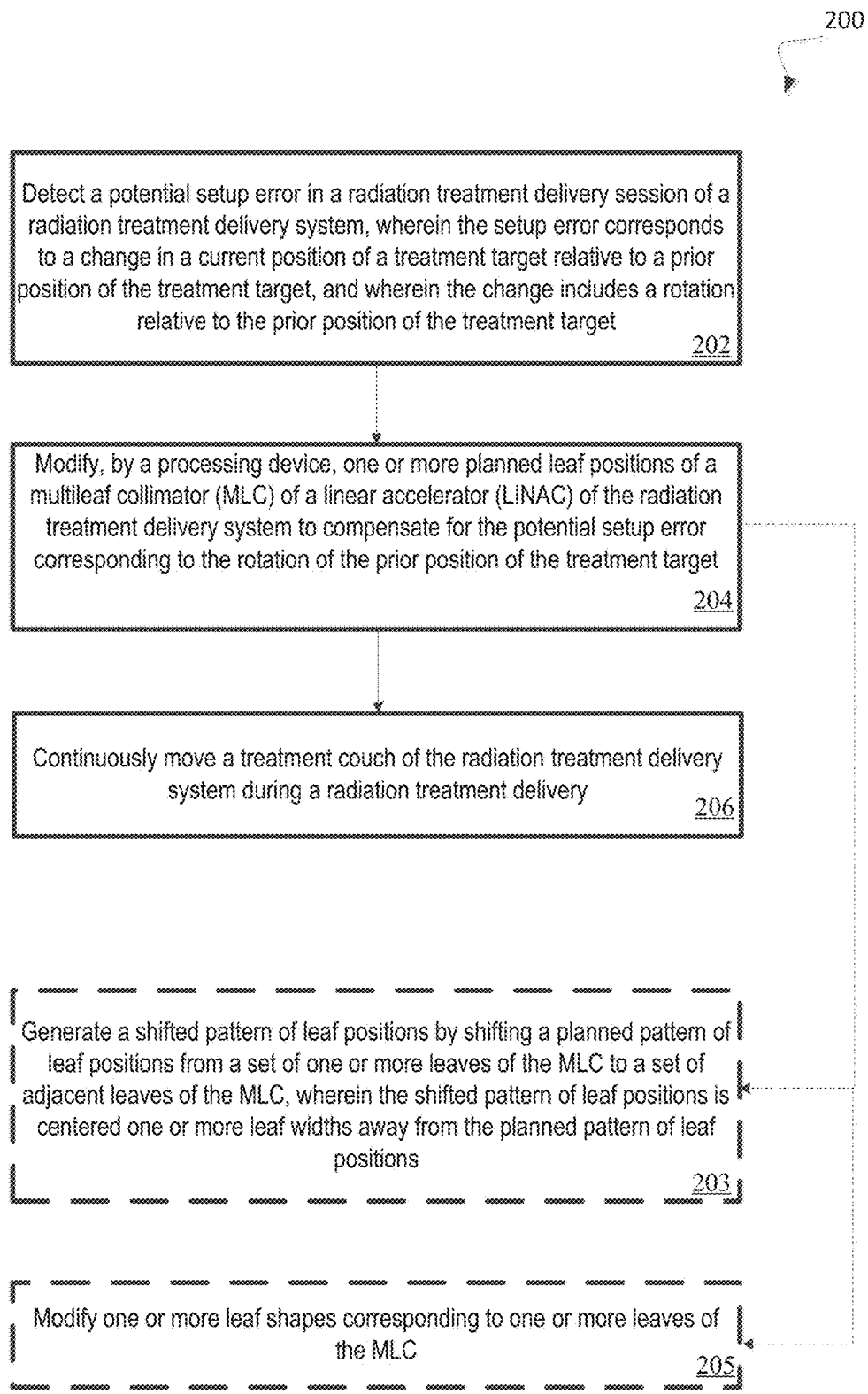
FIG. 2 is a first flowchart illustrating a method for compensating for target rotation with a collimation system, according to embodiments.

FIG. 2 is a first flowchart illustrating a method for compensating for target rotation with a collimation system, according to embodiments. In general, the method 200 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 200 may be performed by processing logic of the radiation treatment system 800 of FIG. 1A.

As shown in FIG. 2, the method 200 may begin at block 202 with the processing logic detecting a potential setup error in a radiation treatment delivery session of a radiation treatment delivery system. The treatment delivery system may be a helical radiation treatment delivery system, a robotic-based LINAC radiation treatment delivery system, or a gantry-based radiation treatment delivery system, or other radiation treatment system.

The setup error corresponds to a change in a current position of a treatment target relative to a prior position of the treatment target. In one embodiment, the current position of the treatment target may be identified in a patient setup image and the prior position of the treatment target may be identified in a treatment planning image. In another embodiment, the current position is identified in a volumetric X-ray image. The volumetric X-ray image may include, for example, kVCT, MVCT, and CBCT images. In another embodiment, the current position is identified in an MR image. In another embodiment, the current position is identified in at least one 2-D X-ray image. For example, this may include kV flat panel images and MV portal images. This may include single images and two or more images (e.g., an orthogonal pair like on CyberKnife). In another embodiment, the current position is identified by optical tracking of externally visible features. For example, this may include surface scanning technologies and tracking discrete point markers located on the patient's surface.

In alternate embodiments the current position may be identified by, but not limited to, pre-treatment kVCT imaging, MVCT imaging, cone-beam (CBCT) imaging, MR imaging, orthogonal flat panel imaging, portal imaging, optical surface tracking, or other method that identifies pre-treatment shifts and rotations of the treatment target.

The change in the current position of the treatment target relative to the prior position may include a rotation (e.g., in the roll, pitch, and/or yaw directions) relative to the prior position of the treatment target. In another embodiment, the change may also, or alternatively, include a translational change in the current position of the treatment target.

At block 204, processing logic modifies, by a processing device, one or more planned leaf positions of a multileaf collimator (MLC) of a linear accelerator (LINAC) of the radiation treatment delivery system to compensate for the potential setup error corresponding to the rotation of the prior position of the treatment target. In one embodiment, the MLC is a binary MLC. In another embodiment, the MLC is a non-binary MLC. In one embodiment, processing logic may perform analysis of the potential setup error to determine how to compensate for the potential setup error. Processing logic may compensate for potential setup errors in a variety of ways.

For example, in one embodiment, processing logic at block 203 may generate a shifted pattern of leaf positions by shifting a planned pattern of leaf positions from a set of one or more leaves of the MLC to a set of adjacent leaves of the MLC. The shifted pattern of leaf positions may be centered one or more leaf widths away from the planned pattern of leaf positions. In this embodiment, the shape defined by the planned leaf pattern may not be changed. Instead, the shape defined by the planned leaf pattern is simply shifted within the MLC, such that the center of the shifted pattern is centered one or more leaf widths away from the center of the planned pattern of leaf positions. In this way, translational movement of the target perpendicular to the movement of leaves in the MLC may be compensated for (e.g., without moving the LINAC). In another embodiment, processing logic may shift the planned pattern of leaf positions and modify leaf open times of leaves in the shifted pattern of leaf positions on a binary MLC.

In another example, in one embodiment, processing logic at block 205 may modify one or more leaf shapes corresponding to one or more leaves of the MLC. In this embodiment, the physical shape defined by the planned leaf pattern may be changed to compensate for the potential translational setup error of the target parallel to the movement of leaves in the MLC. In yet another embodiment, one or more leaf shapes corresponding to one or more leaves of the MLC may be modified in combination with shifting all or a portion of the planned leaf pattern to a new center.

In another embodiment, the amount by which the MLC leaf pattern is shifted may vary as the target is translated through the radiation beam. The amount by which the MLC leaf pattern is shifted corresponds to the apparent translation of the portion of the target that is currently within the radiation field. In this way target rotation may be compensated for as a long target translates through a relatively narrow field, such as happens in a helical fan beam delivery such as on TomoTherapy, without moving the LINAC.

In another embodiment, the MLC fluence pattern that the planned MLC leaf pattern is intended to deliver may be translated and/or rotated and a new MLC leaf pattern may be generated to deliver this new (translated and/or rotated) fluence pattern. In this variation, the MLC leaf pattern may be modified to do more than shift the planned leaf pattern and may modify the beam intensity delivered through each leaf aperture as well. For example, on a system with a fast binary MLC, like a TomoTherapy treatment system, the leaf open time associated to each leaf may be modified to a different leaf open time in addition to being shifted to adjacent leaves. On systems where intensity modulation is accomplished through delivery of multiple discrete segments, each with a different static leaf pattern, these static leaf patterns may be regenerated to account for the translated and/or rotated planned fluence pattern. In this way, translations and rotations may be compensated for with a precision smaller than the width of the MLC leaves.

At block 206, processing logic may optionally continuously move a treatment couch of the radiation treatment delivery system during the radiation treatment delivery session. In another embodiment, the treatment couch of the radiation treatment system is stationary during the modifying of the one or more planned leaf positions of the MLC.

Figure 3:
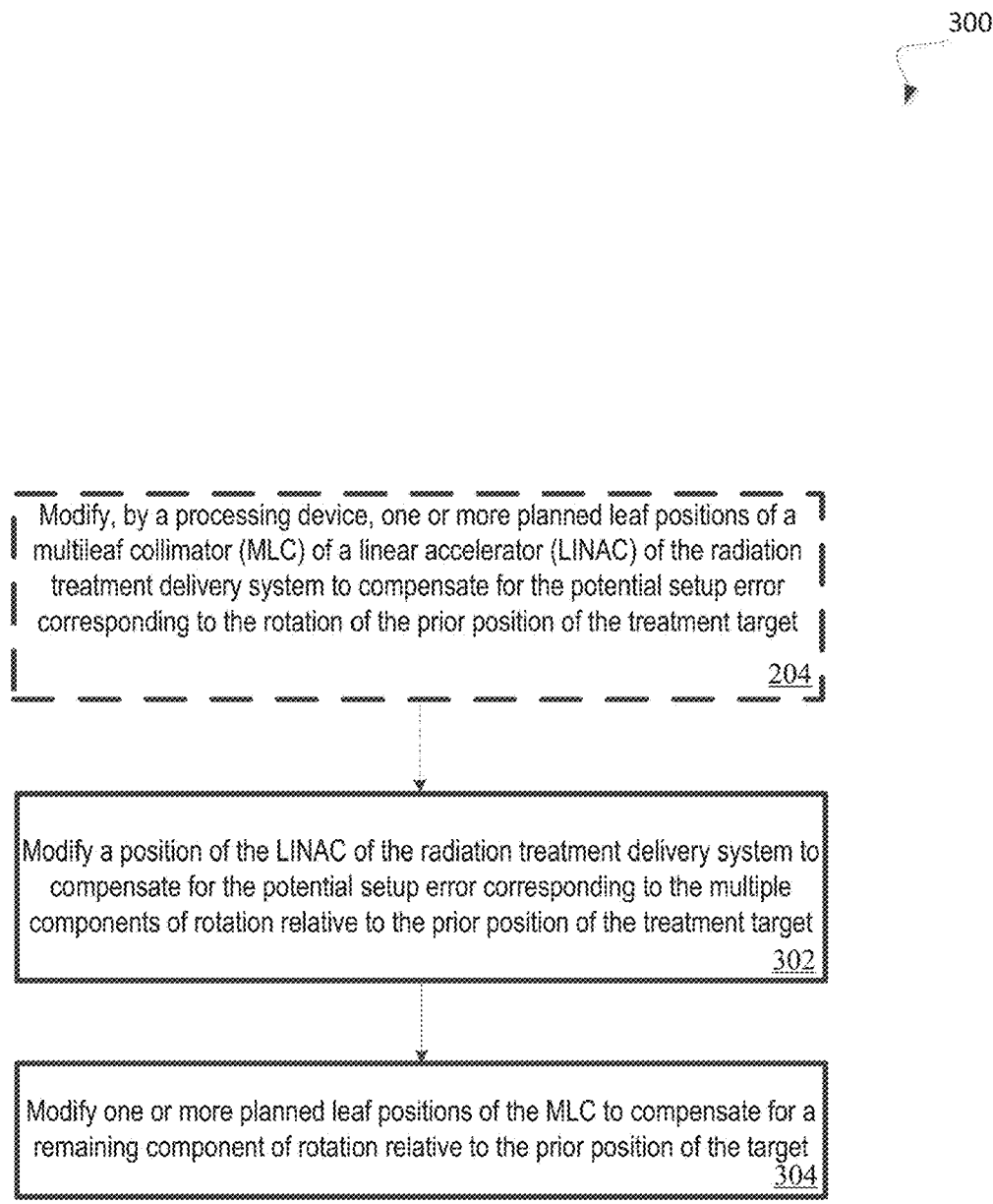
FIG. 3 is a second flowchart illustrating a method for compensating for target rotation with a collimation system, according to embodiments.

FIG. 3 is a second flowchart illustrating a method for compensating for target rotation with a collimation system, according to embodiments. In general, the method 300 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 300 may be performed by processing logic of the radiation treatment system 800 of FIG. 1A.

In one embodiment, the change in current position of a treatment target relative to a prior position of the treatment target (e.g., described with respect to block 202 of FIG. 2) corresponds to multiple components of rotation (e.g., pitch, yaw, and roll) of the prior position of the treatment target. For example, the change may correspond to both the pitch and yaw directions of the treatment target. In another example, the change may correspond to both the roll and yaw directions of the treatment target. In yet another example, the change may correspond to both the pitch and roll directions of the treatment target. In other examples, any other combination of components of rotation may exist.

As shown in FIG. 3, the method 300 may begin at block 302 (optionally continuing from block 204 for FIG. 4), where processing logic modifies a position of the LINAC of the radiation treatment delivery system to compensate for the potential setup error corresponding to one or more of the multiple components of rotation relative to the prior position of the treatment target. For example, in one embodiment, in which the multiple components of rotation include pitch, yaw, and roll, the processing logic may modify a position of the LINAC of the radiation treatment delivery system to compensate for the potential setup error corresponding to the change in roll, leaving the potential setup error corresponding to the change in pitch and yaw uncorrected.

At block 304, processing logic modifies one or more planned leaf positions of the MLC, as described herein, to compensate for at least one remaining component of rotation relative to the prior position of the target. Continuing the above example, the processing logic at block 304 may modify one or more planned leaf positions of the MLC, as described herein, to compensate for the remaining pitch and yaw components of rotation (since roll was compensated for by the LINAC) relative to the prior position of the target.

Figure 4A:
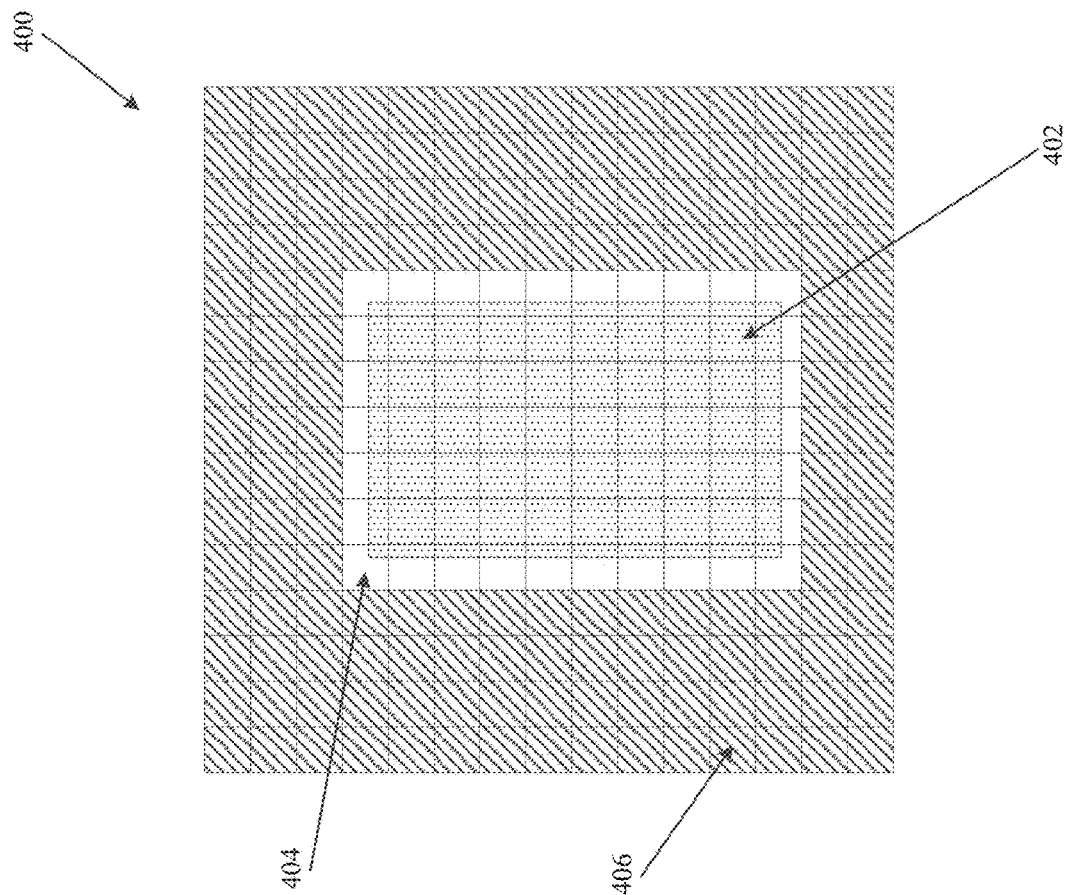
FIG. 4A and FIG. 4B illustrate a yaw correction example, in accordance with embodiments described herein.
Figure 4A:
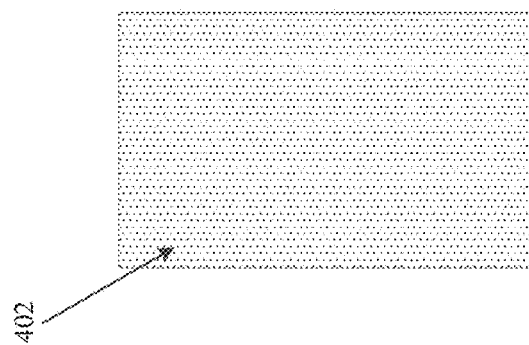
Figure 4B:
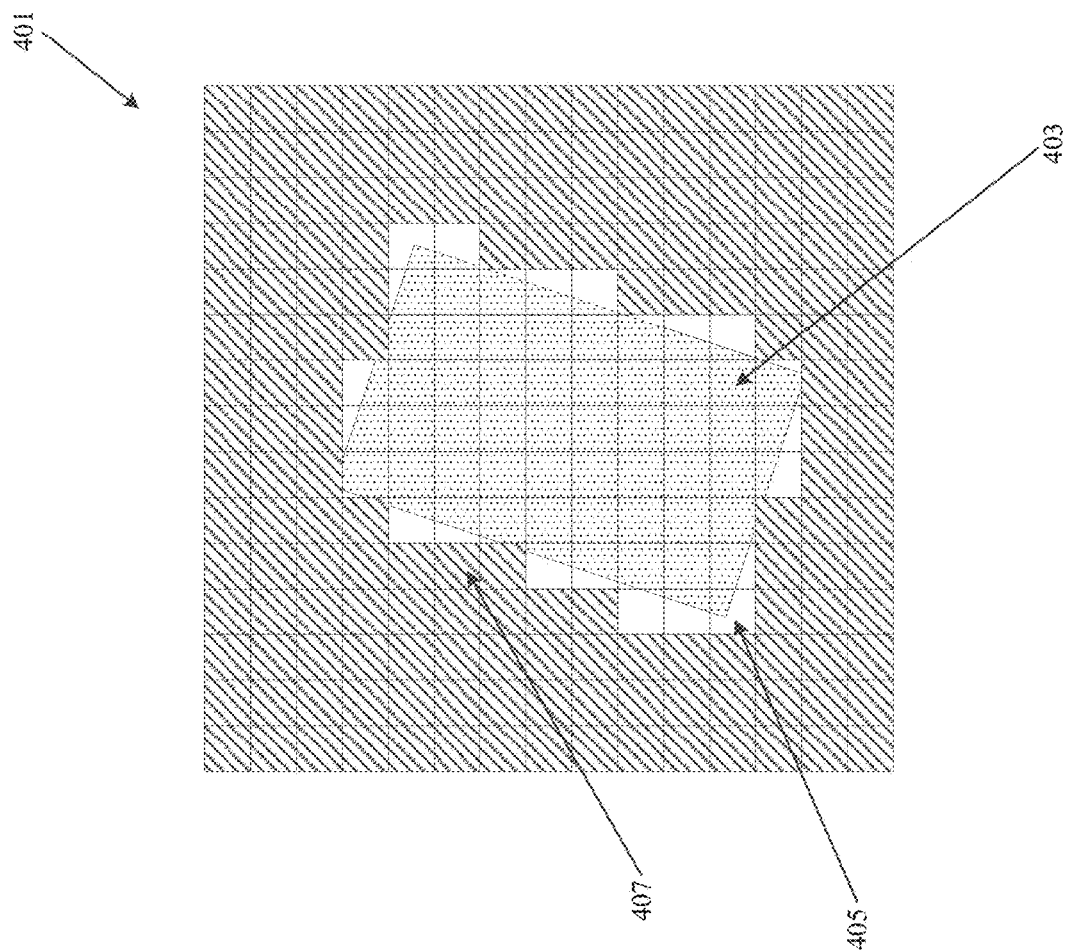
Figure 4B:
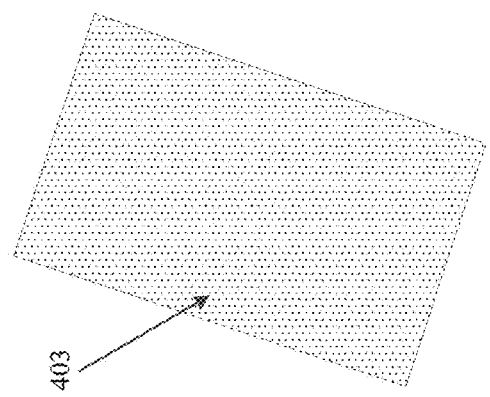

FIG. 4A and FIG. 4B illustrate a yaw correction example, in accordance with embodiments described herein. FIG. 4A and FIG. 4B includes top views of a target 402, and a leaf control sinogram 400, including the target 402, before and after yaw correction is applied, respectively. It should be noted that although the target 402 is depicted as a rectangle, a treatment target may take any form. A rectangle is used to depict the target 402 for convenience and simplicity. In one embodiment, a treatment may be broken up into short projections, where each leaf in the MLC is allowed to open once per projection. The amount of fluence transmitted through each leaf is controlled by the amount of time each leaf is open in each projection. In one embodiment, sinogram 400 represents fluence transmitted through each leaf at each projection.

In the present embodiment, sinogram 400 includes a view of the target 402 and a plurality of active leaves in active projections 404 representing the fluence pattern to the target 402. Sinogram 400 also includes a plurality of inactive leaves and projections 406 representing areas outside of the target 402 not currently receiving fluence. By modifying MLC leaf shapes and patterns to adjust fluence patterns in individual projections, a target area (e.g., target 402) may be treated while minimizing radiation exposure to surrounding areas.

As shown, the MLC leaf pattern may be shifted and/or otherwise modified to generate a different fluence pattern to compensate for a rotated target. For example, the projection-leaf pair 405, which was previously "inactive," may be activated to account for the bottom left corner of the rotated target 403. Projection-leaf pair 407, which was previously active, may be deactivated to compensate for the new position of the rotated target 403. As can be seen, by modifying MLC leaf shapes and patterns to adjust fluence patterns in individual projections, a target area (e.g., target 403) may be treated while minimizing radiation exposure to surrounding areas, even when the target area has rotated in a pitch, yaw, and/or roll direction.

Figure 5:
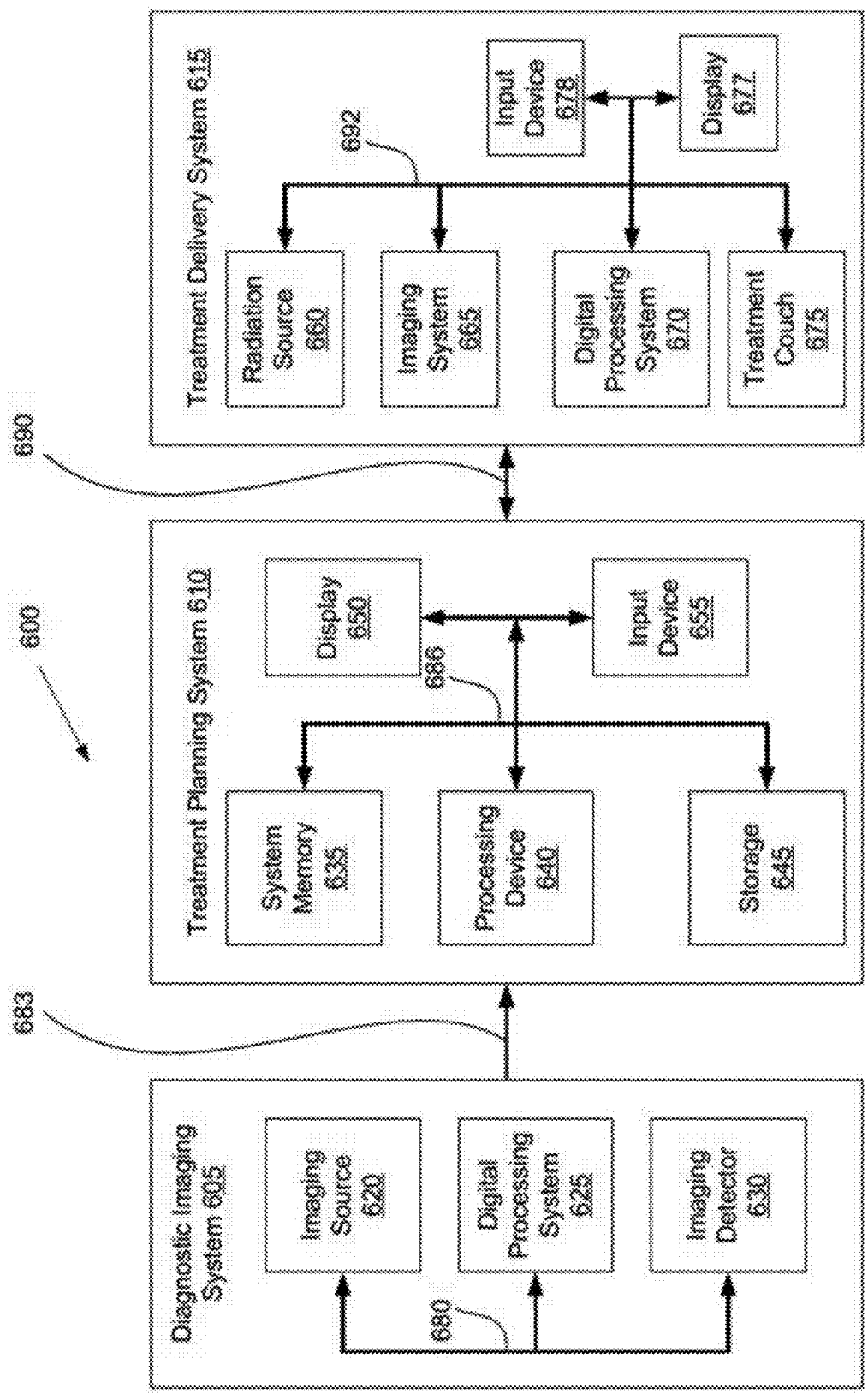
FIG. 5 illustrates examples of different systems that may be used in the generating of the performing of radiation treatment, in accordance with embodiments described herein.

FIG. 5 illustrates examples of different systems 600 within which a set of instructions, for causing the systems to perform any one or more of the methodologies discussed herein, may be executed. In alternative implementations, the machine may be connected (e.g., networked) to other machines in a LAN, an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

As described below and illustrated in FIG. 5, a system 600 may include a diagnostic imaging system 605, a treatment planning system 610, and a treatment delivery system 615. Diagnostic imaging system 605 may be any system capable of producing medical diagnostic images of a patient that may be used for subsequent medical diagnosis, treatment planning, treatment simulation and/or treatment delivery. For example, diagnostic imaging system 605 may be a computed tomography (CT) system, a magnetic resonance imaging (MRI) system, a positron emission tomography (PET) system, a combination of such systems, or the like. For ease of discussion, diagnostic imaging system 605 may be discussed below at times in relation to an x-ray imaging modality. In other embodiments, other imaging modalities such as those discussed above may also be used.

In one embodiment, diagnostic imaging system 605 includes an imaging source 620 to generate an imaging beam (e.g., x-rays) and an imaging detector 630 to detect and receive the beam generated by imaging source 620, or a secondary beam or emission stimulated by the beam from the imaging source (e.g., in an MRI or PET scan).

In one embodiment, imaging source 620 and imaging detector 630 may be coupled to a digital processing system 625 to control the imaging operation and process image data. In one embodiment, diagnostic imaging system 605 may receive imaging commands from treatment delivery system 615 and/or treatment planning system 610.

Diagnostic imaging system 605 includes a bus or other means 680 for transferring data and commands among digital processing system 625, imaging source 620 and imaging detector 630. Digital processing system 625 may include one or more general-purpose processors (e.g., a microprocessor), special purpose processor such as a digital signal processor (DSP) or other type of processing device such as a controller or field programmable gate array (FPGA). Digital processing system 625 may also include other components (not shown) such as memory, storage devices, network adapters and the like. Digital processing system 625 may be configured to generate digital diagnostic images in a standard format, such as the Digital Imaging and Communications in Medicine (DICOM) format, for example. In other embodiments, digital processing system 625 may generate other standard or non-standard digital image formats. Digital processing system 625 may transmit diagnostic image files (e.g., the aforementioned DICOM formatted files) to treatment delivery system 615 over a data link 683, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

In one embodiment, treatment delivery system 615 includes a therapeutic and/or surgical radiation source 660 to administer a prescribed radiation dose to a target volume in conformance with a treatment plan. Treatment delivery system 615 may also include imaging system 665 to perform computed tomography (CT) such as cone beam CT, and images generated by imaging system 665 may be two-dimensional (2D) or three-dimensional (3D).

Treatment delivery system 615 may also include a digital processing system 670 to control radiation source 660, receive and process data from diagnostic imaging system 605 and/or treatment planning system 610, and control a patient support device such as a treatment couch 675. Digital processing system 670 may be connected to or a part of a camera feedback system. Digital processing system 670 may be configured to perform any of the operations described herein. Digital processing system 670 may include a processing device that represents one or more general-purpose processors (e.g., a microprocessor), special purpose processor such as a digital signal processor (DSP) or other type of device such as a controller or field programmable gate array (FPGA). The processing device of digital processing system 670 may be configured to execute instructions to perform the operations described herein.

In one embodiment, digital processing system 670 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 670 may also include a storage device, representing one or more storage devices (e.g., a magnetic disk drive or optical disk drive) for storing information and instructions. The storage device may be used for storing instructions for performing the treatment delivery steps discussed herein. Digital processing system 670 may be coupled to radiation source 660 and treatment couch 675 by a bus 692 or other type of control and communication interface.

In one embodiment, the treatment delivery system 615 includes an input device 678 and a display 677 connected with digital processing system 670 via bus 692. The display 677 can show trend data that identifies a rate of target movement (e.g., a rate of movement of a target volume that is under treatment). The display can also show a current radiation exposure of a patient and a projected radiation exposure for the patient. The input device 678 can enable a clinician to adjust parameters of a treatment delivery plan during treatment.

Treatment planning system 610 includes a processing device 640 to generate and modify treatment plans and/or simulation plans. Processing device 640 may represent one or more general-purpose processors (e.g., a microprocessor), special purpose processor such as a digital signal processor (DSP) or other type of device such as a controller or field programmable gate array (FPGA). Processing device 640 may be configured to execute instructions for performing simulation generating operations and/or treatment planning operations discussed herein.

Treatment planning system 610 may also include system memory 635 that may include a random access memory (RAM), or other dynamic storage devices, coupled to processing device 640 by bus 686, for storing information and instructions to be executed by processing device 640. System memory 635 also may be used for storing temporary variables or other intermediate information during execution of instructions by processing device 640. System memory 635 may also include a read only memory (ROM) and/or other static storage device coupled to bus 686 for storing static information and instructions for processing device 640.

Treatment planning system 610 may also include storage device 645, representing one or more storage devices (e.g., a magnetic disk drive or optical disk drive) coupled to bus 686 for storing information and instructions. Storage device 645 may be used for storing instructions for performing the treatment planning steps discussed herein.

Processing device 640 may also be coupled to a display device 650, such as a cathode ray tube (CRT) or liquid crystal display (LCD), for displaying information (e.g., a 2D or 3D representation of the VOI) to the user. An input device 655, such as a keyboard, may be coupled to processing device 640 for communicating information and/or command selections to processing device 640. One or more other user input devices (e.g., a mouse, a trackball or cursor direction keys) may also be used to communicate directional information, to select commands for processing device 640 and to control cursor movements on display 650.

Treatment planning system 610 may share its database (e.g., data stored in storage 645) with a treatment delivery system, such as treatment delivery system 615, so that it may not be necessary to export from the treatment planning system prior to treatment delivery. Treatment planning system 610 may be linked to treatment delivery system 615 via a data link 690, which in one embodiment may be a direct link, a LAN link or a WAN link.

It should be noted that when data links 683, 686, and 690 are implemented as LAN or WAN connections, any of diagnostic imaging system 605, treatment planning system 610 and/or treatment delivery system 615 may be in decentralized locations such that the systems may be physically remote from each other. Alternatively, any of diagnostic imaging system 605, treatment planning system 610, and/or treatment delivery system 615 may be integrated with each other in one or more systems.

It will be apparent from the foregoing description that aspects of the present disclosure may be embodied, at least in part, in software. That is, the techniques may be carried out in a computer system or other data processing system in response to a processing device 625, 640, or 670 (see FIG. 5), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 670.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.).

For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
    detecting a potential setup error in a radiation treatment delivery session of a radiation treatment delivery system, wherein the setup error corresponds to a change in a current position of a treatment target relative to a prior position of the treatment target, and wherein the change includes a rotation relative to the prior position of the treatment target; and
    modifying, by a processor, one or more planned leaf positions and one or more leaf open times of a binary multileaf collimator (MLC) of the radiation treatment delivery system to compensate for the potential setup error corresponding to the rotation of the prior position of the treatment target while bypassing modifying other parameters associated with the radiation treatment delivery session, wherein modifying the one or more planned leaf positions in the MLC comprises modifying one or more leaf shapes corresponding to one or more leaves of the MLC to compensate for the potential setup error by changing the one or more planned MLC leaf positions during treatment to move an effective location of a treatment beam to change the treatment target orientation.

2. The method of claim 1, wherein modifying the one or more leaf positions in the MLC comprises generating a shifted pattern of leaf positions by shifting a planned pattern of leaf positions from a set of one or more leaves of the MLC to a set of adjacent leaves of the MLC, wherein the shifted pattern of leaf positions is centered one or more leaf widths away from the planned pattern of leaf positions.

3. The method of claim 2, wherein modifying the planned pattern of leaf positions comprises:
shifting the planned pattern of leaf positions; and
modifying leaf open times of leaves in the shifted pattern of leaf positions on the binary MLC.

4. The method of claim 1, wherein the change further corresponds to multiple components of rotation of the prior position of the treatment target, the method further comprising:
modifying a position of a radiation source of the radiation treatment delivery system to compensate for the potential setup error corresponding to at least one of the multiple components of rotation relative to the prior position of the treatment target; and
modifying the one or more planned leaf positions of the MLC to compensate for at least one remaining component of rotation relative to the prior position of the target.

5. The method of claim 1, wherein the radiation treatment delivery system is a helical radiation treatment delivery system.

6. The method of claim 1, wherein the radiation treatment delivery system is a robotic-based LINAC radiation treatment delivery system.

7. The method of claim 1, wherein the radiation treatment delivery system is a gantry-based radiation treatment delivery system.

8. The method of claim 1, further comprising continuously moving a treatment couch of the radiation treatment delivery system during the radiation treatment delivery session.

9. The method of claim 1, wherein a treatment couch of the radiation treatment delivery system is stationary during the modifying of the one or more planned leaf positions of the MLC.

10. The method of claim 1, wherein the prior position is identified in a treatment planning image.

11. The method of claim 1, wherein the current position is identified in a volumetric X-ray image.

12. The method of claim 1, wherein the current position is identified in an MR image.

13. The method of claim 1, wherein the current position is identified in at least one 2-D X-ray image.

14. The method of claim 1, wherein the current position is identified by optical tracking of externally visible features.

15. A radiation treatment delivery system, comprising:
a memory; and
a processor, operatively coupled to the memory, to:
detect a potential setup error in a radiation treatment delivery session, wherein the setup error corresponds to a change in a current position of a treatment target relative to a prior position of the treatment target, and wherein the change includes a rotation relative to the prior position of the treatment target; and
modify one or more planned leaf positions and one or more leaf open times of a multileaf collimator (MLC) of the radiation treatment delivery system to compensate for the potential setup error corresponding to the rotation of the prior position of the treatment target while bypassing modifying other parameters associated with the radiation treatment delivery session, wherein the MLC is a binary MLC.

16. The radiation treatment delivery system of claim 15, wherein to modify the one or more leaf positions in the MLC the processor is to generate a shifted pattern of leaf positions by shifting a planned pattern of leaf positions from a set of one or more leaves of the MLC to a set of adjacent leaves of the MLC, wherein the shifted pattern of leaf positions is centered one or more leaf widths away from the planned pattern of leaf positions.

17. The radiation treatment delivery system of claim 15, wherein to modify the one or more leaf positions in the MLC the processor is to modify one or more leaf shapes corresponding to one or more leaves of the MLC.

18. The radiation treatment delivery system of claim 15, wherein the change further corresponds to multiple components of rotation of the prior position of the treatment target, the processor further to:
modify a position of a radiation source of the radiation treatment delivery system to compensate for the potential setup error corresponding to at least one of the multiple components of rotation relative to the prior position of the treatment target; and
modify the one or more planned leaf positions of the MLC to compensate for at least one remaining component of rotation relative to the prior position of the target.

19. The system of claim 15, wherein the radiation treatment delivery system is one of a helical radiation treatment delivery system, a robotic-based LINAC radiation treatment delivery system, or a gantry-based radiation treatment delivery system.

20. A non-transitory computer readable medium comprising instructions that, when executed by a processor of a radiation treatment delivery system, cause the processor to:
detect a potential setup error in a radiation treatment delivery session, wherein the setup error corresponds to a change in a current position of a treatment target relative to a prior position of the treatment target, and wherein the change includes a rotation relative to the prior position of the treatment target; and
modify, by the processor, one or more planned leaf positions and one or more leaf open times of a binary multileaf collimator (MLC) of the radiation treatment delivery system to compensate for the potential setup error corresponding to the rotation of the prior position of the treatment target while bypassing modifying other parameters associated with the radiation treatment delivery session, wherein to modify the one or more planned leaf positions in the MLC, the processor to:
modify one or more leaf shapes corresponding to one or more leaves of the MLC to compensate for the potential setup error by changing the one or more planned MLC leaf positions during treatment to move an effective location of a treatment beam to change the treatment target orientation.

21. The non-transitory computer readable medium of claim 20, wherein the radiation treatment delivery system is one of a helical radiation treatment delivery system, a robotic-based LINAC radiation treatment delivery system, or a gantry-based radiation treatment delivery system.

22. The non-transitory computer readable medium of claim 20, the processor further to continuously move a treatment couch of the radiation treatment delivery system during a radiation treatment delivery session.

23. The non-transitory computer readable medium of claim 20, wherein a treatment couch of the radiation treatment delivery system is stationary during the modifying of the one or more planned leaf positions of the MLC.

24. The non-transitory computer readable medium of claim 20, wherein the prior position is identified in a pre-treatment planning image and wherein the current position is identified in a patient setup image.

* * * * *